(12) United States Patent
Seto et al.

(10) Patent No.: US 7,429,356 B2
(45) Date of Patent: Sep. 30, 2008

(54) EXTRACTING APPARATUS

(75) Inventors: Yoshihiro Seto, Minamiashigara (JP);
Takahiro Miyato, Minamiashigara (JP);
Keiichi Fujimoto, Minamiashigara (JP)

(73) Assignee: FUJIFILM Corporation, Tokyo (JP)

( * ) Notice: Subject to any disclaimer, the term of this patent is extended or adjusted under 35 U.S.C. 154(b) by 502 days.

(21) Appl. No.: 10/920,447

(22) Filed: Aug. 18, 2004

(65) Prior Publication Data

US 2005/0045538 A1    Mar. 3, 2005

(30) Foreign Application Priority Data

Aug. 19, 2003  (JP) ............................. 2003-295084
Aug. 19, 2003  (JP) ............................. 2003-295085
Oct. 17, 2003  (JP) ............................. 2003-357674

(51) Int. Cl.
*G01N 35/10* (2006.01)

(52) U.S. Cl. ...................... 422/63; 210/258; 210/416.1; 422/69; 422/101; 422/102; 422/104

(58) Field of Classification Search .............. 210/416.1, 210/511, 656, 660, 634, 767, 258; 422/69, 422/70, 63–65, 99–104, 68.1; 436/43–45, 436/53, 174–180, 161; 435/6, 287.1, 287.2, 435/287.7

See application file for complete search history.

(56) References Cited

U.S. PATENT DOCUMENTS 4,948,564 A * 8/1990 Root et al. .................. 422/101

| 5,114,858 | A |  | 5/1992 | Williams et al. |
| 5,645,723 | A |  | 7/1997 | Fujishiro et al. |
| 6,270,970 | B1 | * | 8/2001 | Smith et al. ..................... 435/6 |
| 6,451,260 | B1 | * | 9/2002 | Dusterhoft et al. ......... 422/68.1 |
| 6,783,732 | B2 | * | 8/2004 | Madden et al. ............... 422/63 |
| 6,812,012 | B1 | * | 11/2004 | Hattori et al. ............... 435/189 |
| 2001/0016178 | A1 |  | 8/2001 | Woodhead et al. |
| 2003/0170664 | A1 |  | 9/2003 | Mori et al. |
| 2004/0126890 | A1 | * | 7/2004 | Gjerde et al. ................. 436/53 |

FOREIGN PATENT DOCUMENTS

| EP | 0 288 425 A | 10/1988 |
| FR | 2 761 373 A | 10/1988 |
| JP | 3058342 B2 | 4/2000 |

* cited by examiner

*Primary Examiner*—Joseph W Drodge
(74) *Attorney, Agent, or Firm*—Sughrue Mion, PLLC

(57) ABSTRACT

A loading mechanism holds at least one extracting cartridge provided with a filter member, at least one waste liquid vessel for accommodating a discharged liquid of a sample liquid and a discharged liquid of a washing liquid, which discharged liquids have been discharged from the extracting cartridge, and at least one recovery vessel for accommodating a recovery liquid, which contains a recovered nucleic acid and has been discharged from the extracting cartridge. A pressurized air supplying mechanism introduces pressurized air into the extracting cartridge. A liquid injecting mechanism injects each of the washing liquid and the recovery liquid into the extracting cartridge.

15 Claims, 7 Drawing Sheets

EXTRACTING APPARATUS

BACKGROUND OF THE INVENTION

1. Field of the Invention

This invention relates to an extracting apparatus for extracting a predetermined substance such as a nucleic acid from a sample liquid by use of at least one extracting cartridge provided with a filter member.

2. Description of the Related Art

As extracting methods, for example in techniques for extracting a nucleic acid, a centrifugal technique, a technique utilizing magnetic beads, a technique utilizing a filter, and the like, have heretofore been known.

For example, there has been proposed a nucleic acid extracting apparatus utilizing filters. With the proposed nucleic acid extracting apparatus, a plurality of filter tubes, each of which accommodates a filter therein, are set on a rack, and sample liquids are respectively injected into the filter tubes. Also, a region around a bottom of the rack is closed with an air chamber via a sealing material, and a pressure within the air chamber is reduced. Areas within all of the filter tubes are thus simultaneously subjected to suction from discharging sides of the filter tubes, and the sample liquids contained in the filter tubes are thus caused to pass through the filters of the filter tubes. Nucleic acids contained in the sample liquids are thus adsorbed to the filters of the filter tubes. Thereafter, a washing liquid and an eluting liquid are successively injected into the filter tubes and subjected to suction at a reduced pressure. The nucleic acids having been adsorbed to the filters of the filter tubes are thus washed with the washing liquid and eluted from the filters. (The aforesaid nucleic acid extracting apparatus utilizing filters is described in, for example, U.S. Pat. No. 5,645,723.)

As described above, a separation purification method of a nucleic acid, comprising the step of using a predetermined filter for separating and recovering the sample liquid after the nucleic acid contained in the sample liquid is adsorbed to the filter, is disclosed in U.S. patent laid-open No. 20030170664. Further, a method for extracting by injecting the sample liquid into the separation purification unit including the filter and pressurizing the sample liquid is adopted.

However, the conventional nucleic acid extracting apparatus described above has the problems in that, in cases where the nucleic acid extracting apparatus has a large size so as to be appropriate for analyses of large amounts of samples and in cases where the number of the samples is small, and the frequency of analyses is low, the cost of the nucleic acid extracting apparatus is not capable of being kept low, and the processing efficiency is not capable of being kept high.

Also, as for nucleic acid extracting apparatuses, it is desired that the processing is capable of being performed quickly and efficiently without any contamination occurring, and that the sizes of the nucleic acid extracting apparatuses are capable of being kept small. However, the problems described below occur with the nucleic acid extracting apparatus proposed in U.S. Pat. No. 5,645,723.

Specifically, with a nucleic acid extracting apparatus, in which the areas within all of the filter tubes are simultaneously subjected to suction as in the cases of the nucleic acid extracting apparatus proposed in U.S. Pat. No. 5,645,723, in cases where the sample liquids have different characteristics as in the cases of sampled whole blood, at the time at which the suction with respect to a certain filter tube is completed, and the resistance against the suction with respect to the certain filter tube disappears, the effect of the reduced pressure acting upon the other filter tubes becomes small. As a result, the problems often occur in that the processing on sample liquids having a comparatively high viscosity is not capable of being completed. In cases where the capacity of the reduced pressure is increased in order to prevent the aforesaid problems from occurring, the size of the nucleic acid extracting apparatus is not capable of being kept small. Also, due to a large volume of the reduced pressure, a long time is required to obtain the reduced pressure. Further, it is not always possible to detect the completion of the discharging of all of the sample liquids. Therefore, the setting time is not capable of being kept short, and the processing efficiency is not capable of being enhanced. Furthermore, the problems occur in that a sample liquid having a low viscosity is vigorously discharged from the filter tube, and a bubble-like splash of the sample liquid clings to an adjacent filter tube and an adjacent area of the rack and causes contamination to occur. As a result, the accuracy of the analysis is not capable of being kept high.

A method for recovering the liquid by adsorbing the nucleic acid to the filter by pressurization is disclosed in U.S. patent laid-open No. 20030170664. However, a specific extracting apparatus is not disclosed. In the extracting apparatus which adopts the pressurization method, problems will arise in its pressurization control method. Problems will also arise in contamination due to scattering of the discharged liquid during pressurization, reliability in sealing, or the like.

SUMMARY OF THE INVENTION

The primary object of the present invention is to provide an extracting apparatus, which is capable of automatically performing quick and efficient extraction of a nucleic acid from a sample liquid and is capable of being kept small in size.

Another object of the present invention is to provide an extracting apparatus, wherein problems with regard to contamination are capable of being prevented from occurring, and extraction accuracy is capable of being kept high.

The present invention provides an extracting apparatus for performing an extracting operation by use of at least one extracting cartridge provided with a filter member, the extracting operation comprising:

injecting a sample liquid, which contains a predetermined substance, into the extracting cartridge, pressurizing an area within the extracting cartridge into which the sample liquid has been injected, the sample liquid being thereby caused to pass through the filter member of the extracting cartridge under pressure, the predetermined substance contained in the sample liquid being thus adsorbed to the filter member of the extracting cartridge, and recovering an extracted component together with the recovery liquid, the apparatus comprising:

i) a loading mechanism for holding the at least one extracting cartridge, at least one waste liquid vessel for accommodating a discharged liquid of the sample liquid and at least one recovery vessel for accommodating the recovery liquid, which contains the extracted component, ii) a pressurized air supplying mechanism for introducing pressurized air into the at least one extracting cartridge, and iii) a liquid injecting mechanism for injecting each of the recovery liquid into the at least one extracting cartridge.

The extracting apparatus in accordance with the present invention should preferably be modified such that the loading mechanism comprises:

a) a stand, which is loaded on an apparatus main body, b) a cartridge holder, which is supported for vertical movement by the stand and holds the at least one extracting cartridge, and c) a vessel holder, which holds the at least one waste liquid vessel and the at least one recovery vessel at positions below the cartridge holder such that the position of the at least one waste liquid vessel with respect to the at least one extracting cartridge and the position of the at least one recovery vessel with respect to the at least one extracting cartridge are capable of being changed over.

Also, the extracting apparatus in accordance with the present invention should preferably be modified such that the pressurized air supplying mechanism comprises:

a) at least one air nozzle, which jets out pressurized air from a bottom end, b) a pressurizing head, which supports the at least one air nozzle and vertically moves the at least one air nozzle with respect to the at least one extracting cartridge having been held by the cartridge holder, and c) position adjusting means, which is fitted to the pressurizing head and adjusts the position of the at least one extracting cartridge in a rack of the loading mechanism.

Further, the extracting apparatus in accordance with the present invention should preferably be modified such that the liquid injecting mechanism comprises:

a) a recovery liquid injecting nozzle, from which the recovery liquid is injected into the at least one extracting cartridge, b) a nozzle moving base, which holds the recovery liquid injecting nozzle and is capable of moving above the at least one extracting cartridge having been held by the loading mechanism, and c) a recovery liquid supplying pump, which sucks up the recovery liquid from a recovery liquid bottle that accommodates the recovery liquid therein, and which supplies the recovery liquid into the recovery liquid injecting nozzle.

Furthermore, the extracting apparatus in accordance with the present invention should preferably be modified such that, the loading mechanism comprises:

a) a stand, which is loaded on an apparatus main body, b) a cartridge holder, which is supported for vertical movement by the stand and holds the at least one extracting cartridge, and c) a vessel holder, which holds the at least one waste liquid vessel and the at least one recovery vessel at positions below the cartridge holder such that the position of the at least one waste liquid vessel with respect to the at least one extracting cartridge and the position of the at least one recovery vessel with respect to the at least one extracting cartridge are capable of being changed over, the pressurized air supplying mechanism comprises:

a) at least one air nozzle, which jets out pressurized air from a bottom end, b) a pressurizing head, which supports the at least one air nozzle and vertically moves the at least one air nozzle with respect to the at least one extracting cartridge having been held by the cartridge holder, and c) position adjusting means, which is fitted to the pressurizing head and adjusts the position of the at least one extracting cartridge in a rack of the loading mechanism, and the liquid injecting mechanism comprises:

a) a recovery liquid injecting nozzle, from which the recovery liquid is injected into the at least one extracting cartridge, b) a nozzle moving base, which holds the recovery liquid injecting nozzle and is capable of moving above the at least one extracting cartridge having been held by the loading mechanism, and c) a recovery liquid supplying pump, which sucks up the recovery liquid from a recovery liquid bottle that accommodates the recovery liquid therein, and which supplies the recovery liquid into the recovery liquid injecting nozzle.

Furthermore, the extracting apparatus in accordance with the present invention should preferably be modified such that, the apparatus comprises a scattering prevention means for preventing scattering of the discharged liquid from a discharge bottom end of the extracting cartridge at the time at which the pressurized air is to be supplied into the at least one extracting cartridge in order to discharge the discharged liquid from the at least one extracting cartridge into the at least one waste liquid vessel.

Furthermore, the extracting apparatus in accordance with the present invention should preferably be modified such that, at the time at which the pressurized air is to be supplied into the at least one extracting cartridge in order to discharge the discharged liquid from the at least one extracting cartridge into the at least one waste liquid vessel, a discharging bottom end of the at least one extracting cartridge is inserted by a predetermined length into the at least one waste liquid vessel to prevent scattering of the discharged liquid.

Also, the extracting apparatus in accordance with the present invention should preferably be modified such that, at the time at which the sample liquid or the washing liquid is to be injected into the at least one extracting cartridge, the at least one extracting cartridge is located just above the at least one waste liquid vessel, and/or at the time at which the recovery liquid is to be injected into the at least one extracting cartridge, the at least one extracting cartridge is located just above the at least one recovery vessel.

Further, the extracting apparatus in accordance with the present invention should preferably be modified such that the loading mechanism comprises:

a) a cartridge holder, which holds the at least one extracting cartridge and is capable of moving vertically, and b) a vessel holder, which holds the at least one waste liquid vessel and the at least one recovery vessel at positions below the cartridge holder such that the position of the at least one waste liquid vessel with respect to the at least one extracting cartridge and the position of the at least one recovery vessel with respect to the at least one extracting cartridge are capable of being changed over, the pressurized air supplying mechanism comprises:

a) a pressurizing head for vertically moving at least one air nozzle, which jets out pressurized air from a bottom end, and b) push pins, which are fitted to the pressurizing head and are capable of coming into abutment with the cartridge holder of the loading mechanism, and the pressurized air supplying mechanism operates such that:

at the time at which the pressurized air is to be supplied into the at least one extracting cartridge, the push pins come into abutment with the cartridge holder of the loading mechanism in accordance with a downward movement of the pressurizing head in order to regulate the position of the cartridge holder of the loading mechanism and in order to push the cartridge holder, and thereafter the at least one air nozzle is pushed against the at least one extracting cartridge, which has been held by the cartridge holder.

Furthermore, the extracting apparatus in accordance with the present invention should preferably be modified such that the processing step concerning the injection of the liquid into the at least one extracting cartridge, which processing step is performed after the adsorption processing of the sample liquid, is performed while the discharging bottom end of the at least one extracting cartridge is being kept in the state in which the discharging bottom end of the at least one extracting cartridge is inserted into the at least one waste liquid vessel.

Also, the predetermined substance is a nucleic acid and the filter member of the at least one extracting cartridge should preferably be constituted of a porous film capable of adsorbing the nucleic acid with an interaction other than interactions in which an ionic bond takes part. For example, the filter member of the at least one extracting cartridge may be constituted of a porous film of an organic material having a hydroxyl group. Alternatively, the filter member of the at least one extracting cartridge may be constituted of a porous film of a mixture of acetylcelluloses having different acetyl values. As another alternative, the filter member of the at least one extracting cartridge may be constituted of a porous film of a regenerated cellulose. As a further alternative, the filter member of the at least one extracting cartridge may be constituted of a porous film of an organic material obtained from saponification of a mixture of acetylcelluloses having different acetyl values. As a still further alternative, the filter member of the at least one extracting cartridge may be constituted of a porous film of an inorganic material containing a silica compound. In such cases, the filter member may be, for example, a glass filter.

As described above, the extracting apparatus in accordance with the present invention comprises the loading mechanism for holding the at least one extracting cartridge, the at least one waste liquid vessel, and the at least one recovery vessel. The extracting apparatus in accordance with the present invention also comprises the pressurized air supplying mechanism for introducing the pressurized air into the at least one extracting cartridge, and the liquid injecting mechanism for injecting each of the recovery liquid into the at least one extracting cartridge. The extracting apparatus in accordance with the present invention is capable of performing the extracting operation comprising:

injecting the sample liquid, which contains the predetermined substance, into the extracting cartridge provided with the filter member, pressurizing the area within the extracting cartridge into which the sample liquid has been injected, the sample liquid being thereby caused to pass through the filter member of the extracting cartridge under pressure, the predetermined substance contained in the sample liquid being thus adsorbed to the filter member of the extracting cartridge, and recovering an extracted component together with the recovery liquid.

The extracting apparatus in accordance with the present invention is thus capable of performing quick and efficient extraction of the predetermined substance from the sample liquid and is capable of being kept small in size.

The extracting apparatus in accordance with the present invention may be modified such that the loading mechanism comprises: (a) the stand, which is loaded on the apparatus main body, (b) the cartridge holder, which is supported for vertical movement by the stand and holds the at least one extracting cartridge, and (c) the vessel holder, which holds the at least one waste liquid vessel and the at least one recovery vessel at positions below the cartridge holder such that the position of the at least one waste liquid vessel with respect to the at least one extracting cartridge and the position of the at least one recovery vessel with respect to the at least one extracting cartridge are capable of being changed over. With the modification described above, the setting of the extracting cartridge, the setting of the waste liquid vessel, the setting of the recovery vessel, and the changeover between the waste liquid vessel and the recovery vessel are capable of being performed easily.

Also, the extracting apparatus in accordance with the present invention may be modified such that the pressurized air supplying mechanism comprises: (a) the at least one air nozzle, which jets out the pressurized air from the bottom end, (b) the pressurizing head, which supports the at least one air nozzle and vertically moves the at least one air nozzle with respect to the at least one extracting cartridge having been held by the cartridge holder, and (c) the position adjusting means, which is fitted to the pressurizing head and adjusts the position of the at least one extracting cartridge in the rack of the loading mechanism. With the modification described above, the supply of the pressurized air is capable of being performed reliably with the simple mechanism.

Further, the extracting apparatus in accordance with the present invention may be modified such that the liquid injecting mechanism comprises: (a) the recovery liquid injecting nozzle, from which the recovery liquid is injected into the at least one extracting cartridge, (b) the nozzle moving base, which holds the recovery liquid injecting nozzle and is capable of moving above the at least one extracting cartridge having been held by the loading mechanism, and (c) the recovery liquid supplying pump, which sucks up the recovery liquid from the recovery liquid bottle that accommodates the recovery liquid therein, and which supplies the recovery liquid into the recovery liquid injecting nozzle. With the modification described above, the injection of the injection of the recovery liquid is capable of being performed successively with the simple mechanism.

Furthermore, the extracting apparatus in accordance with the present invention may be modified such that, at the time at which the pressurized air is to be supplied into the at least one extracting cartridge in order to discharge the discharge from the at least one extracting cartridge into the at least one waste liquid vessel, the discharging bottom end of the at least one extracting cartridge is inserted by the predetermined length into the at least one waste liquid vessel.

With the modification described above, scattering of the discharged liquid is capable of being prevented from occurring at the time of the pressurization. Also, in cases where the extraction processing is performed for a plurality of sample liquids and in cases where continuous processing is performed, the problems with regard to the contamination due to clinging and inclusion of different sample liquid constituents are capable of being prevented from occurring, and the extraction accuracy is capable of being kept high.

Also, the extracting apparatus in accordance with the present invention may be modified such that, at the time at which the sample liquid is to be injected into the at least one extracting cartridge, the at least one extracting cartridge is located just above the at least one waste liquid vessel.

With the modification described above, during the liquid injection and during other processing steps, the liquid dropping from the extracting cartridge is capable of being reliably accommodated within the waste liquid vessel. Therefore, contamination of the apparatus is capable of being prevented from occurring. Also, the liquid dropping from the extracting cartridge is capable of being prevented from clinging to the next extracting cartridge or the next recovery vessel, and the problems with regard to the contamination are thus capable of being prevented from occurring.

Further, the extracting apparatus in accordance with the present invention may be modified such that the pressurized air supplying mechanism comprises: (a) the pressurizing head for vertically moving at least one air nozzle, which jets out pressurized air from the bottom end, and (b) the push pins, which are fitted to the pressurizing head and are capable of coming into abutment with the cartridge holder of the loading mechanism, and the pressurized air supplying mechanism operates such that:

at the time at which the pressurized air is to be supplied into the at least one extracting cartridge, the push pins come into abutment with the cartridge holder of the loading mechanism in accordance with the downward movement of the pressurizing head in order to regulate the position of the cartridge holder of the loading mechanism and in order to push the cartridge holder, and thereafter the at least one air nozzle is pushed against the at least one extracting cartridge, which has been held by the cartridge holder.

With the modification described above, the air nozzle is capable of being pushed at an accurate position against the extracting cartridge, and the sealed state of the extracting cartridge is capable of being obtained reliably. Therefore, the supply of the pressurized air is capable of being performed reliably.

Furthermore, the extracting apparatus in accordance with the present invention may be modified such that the processing step, which is performed after the adsorption processing of the sample liquid, is performed while the discharging bottom end of the at least one extracting cartridge is being kept in the state in which the discharging bottom end of the at least one extracting cartridge is inserted into the at least one waste liquid vessel. With the modification described above, during the processing step, the extracting cartridge does not undergo vertical movement with respect to the waste liquid vessel. Therefore, the problems are capable of being reliably prevented from occurring in that the liquid discharged from the extracting cartridge leaks to the exterior of the waste liquid vessel.

Also, the predetermined substance is the nucleic acid and the filter member of the at least one extracting cartridge may be constituted of the porous film capable of adsorbing the nucleic acid with an interaction other than interactions in which the ionic bond takes part. In such cases, the adsorption and the recovery of the sample liquid from the sample liquid are capable of being performed appropriately.

DESCRIPTION OF THE PREFERRED EMBODIMENTS

The present invention will hereinbelow be described in further detail with reference to the accompanying drawings.

Figure 1:
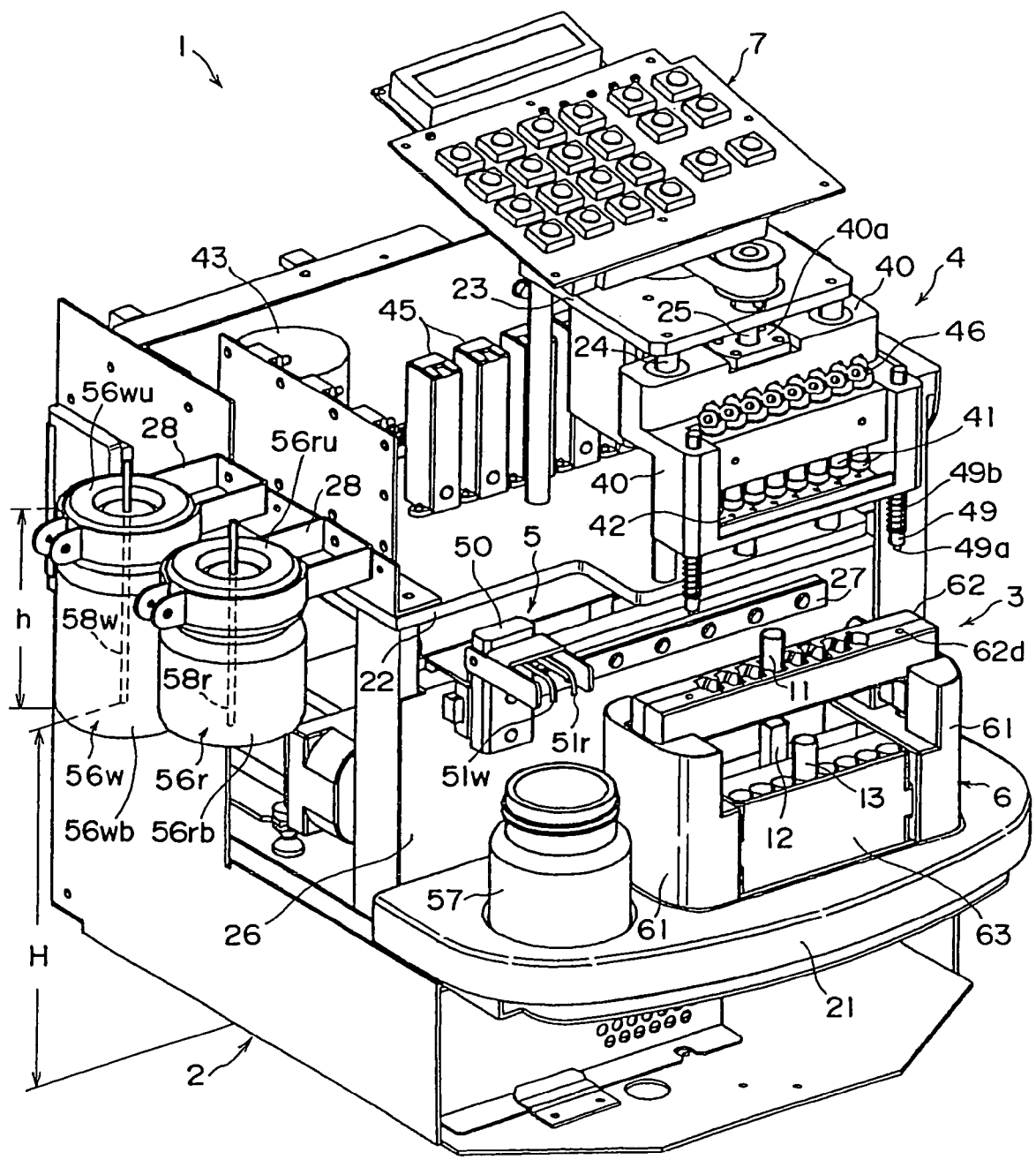
FIG. 1 is a perspective view showing an embodiment of the nucleic acid extracting apparatus in accordance with the present invention with a cover being removed.
Figure 2:
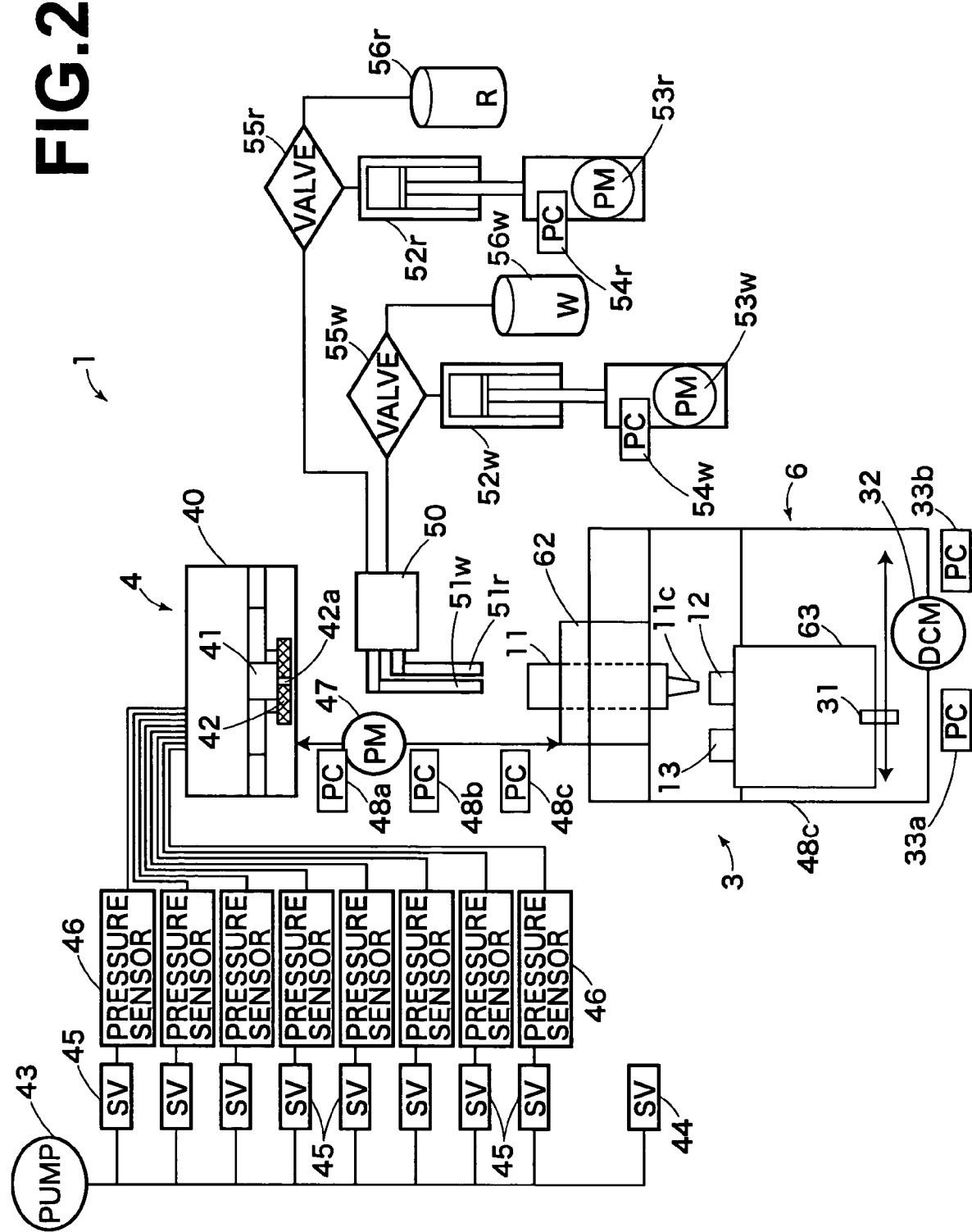
FIG. 2 is a block diagram showing mechanisms of the nucleic acid extracting apparatus of FIG. 1.
Figure 3:
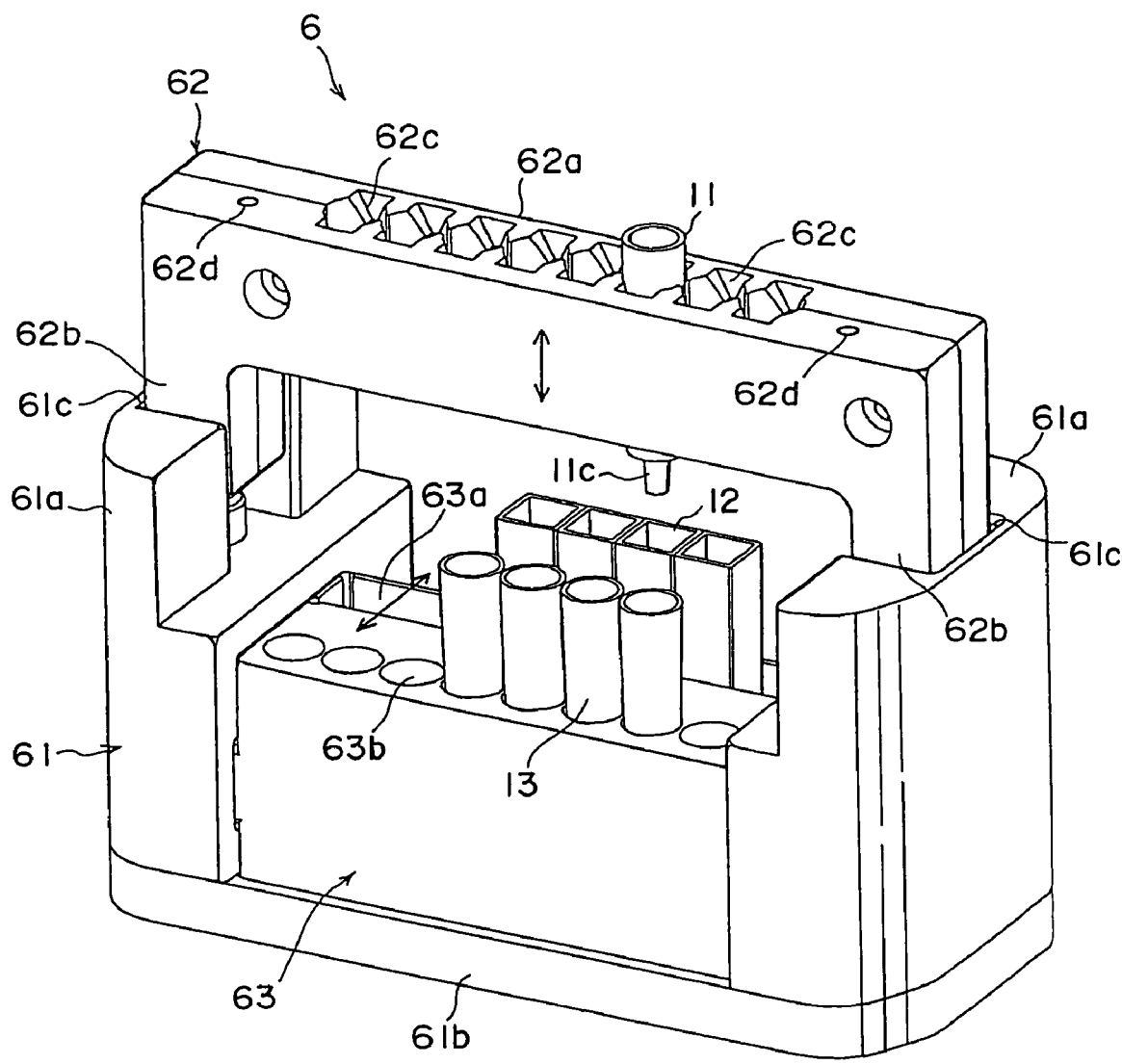
FIG. 3 is a perspective view showing a rack of a loading mechanism.
Figure 4:
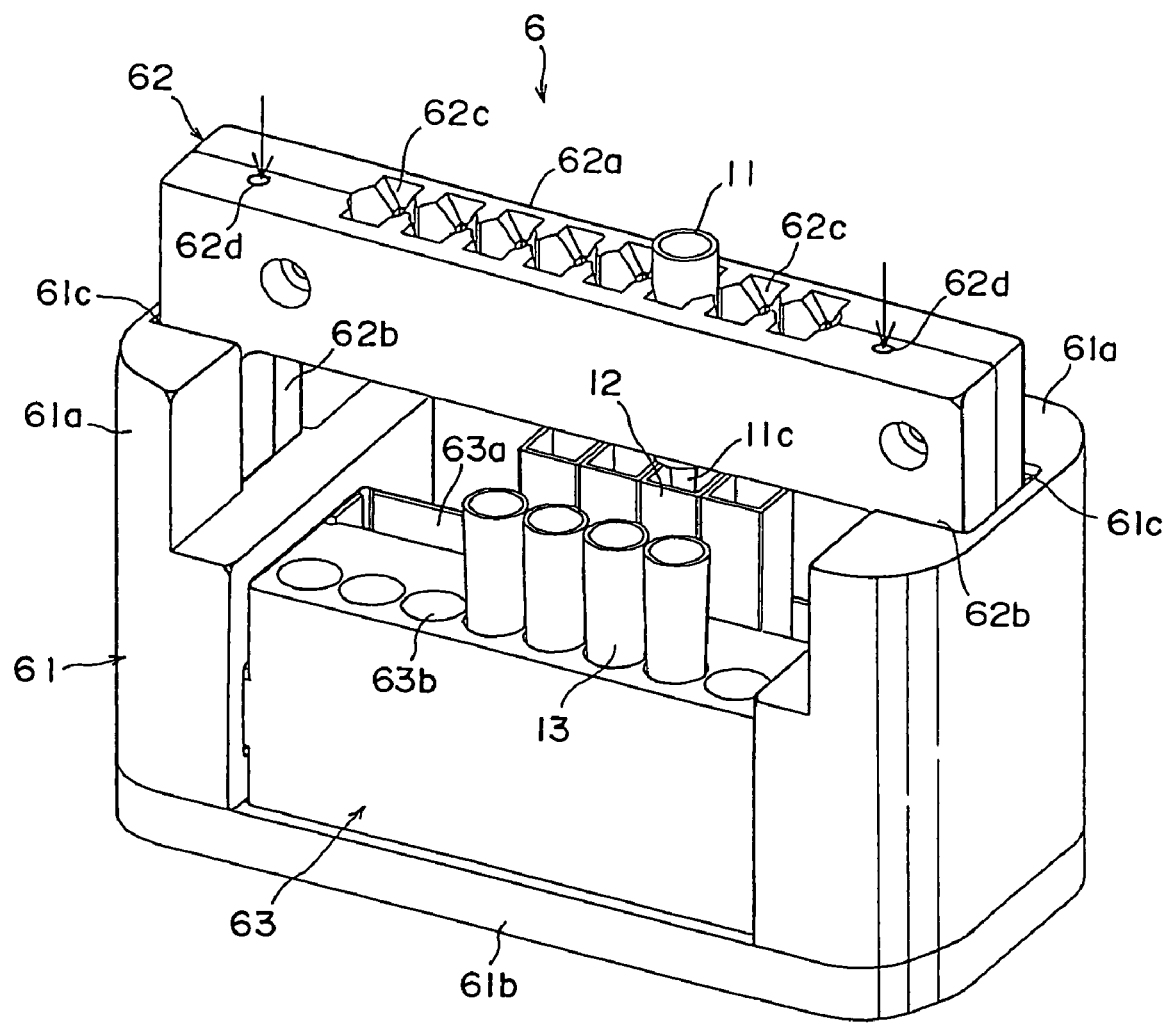
FIG. 4 is a perspective view showing the rack of FIG. 3 in the state in which the rack is being used.

FIG. 1 is a perspective view showing an embodiment of the nucleic acid extracting apparatus in accordance with the present invention with a cover being removed. FIG. 2 is a block diagram showing mechanisms of the nucleic acid extracting apparatus of FIG. 1. FIG. 3 is a perspective view showing a rack of a loading mechanism. FIG. 4 is a perspective view showing the rack of FIG. 3 in the state in which the rack is being used. FIGS. 5A to 5G are flow diagrams showing an extracting operation. FIG. 6 is a perspective view showing an extracting cartridge.

A nucleic acid extracting apparatus 1 illustrated in FIG. 1 extracts a nucleic acid from a sample liquid by use of an extracting cartridge (a filter cartridge) 11 illustrated in FIG. 6. As illustrated in FIG. 6, the extracting cartridge 11 comprises a tubular main body 11a having an opening at its top end. The extracting cartridge 11 also comprises a filter member 11b, which is held within the tubular main body 11a and at a bottom of the tubular main body 11a. Part of the tubular main body 11a, which part is lower than the filter member 11b, is formed in a funnel-like shape. Also, a discharging bottom end 11c, which has a nozzle-like shape having a reduced diameter, protrudes by a predetermined length from a center region of the bottom of the funnel-like part of the tubular main body 11a. Further, vertically extending protrusions 11d, 11d are formed on opposite sides of a side wall of the tubular main body 11a. As will be described later, a sample liquid, a washing liquid, or a recovery liquid is injected through the top opening of the tubular main body 11a into the extracting cartridge 11. Also, pressurized air is introduced through the top opening of the tubular main body 11a into the extracting cartridge 11 in order to cause the sample liquid, the washing liquid, or the recovery liquid to pass through the filter member 11b and to discharge the liquid through the discharging bottom end 11c into one of waste liquid vessels 12, 12, . . . or recovery vessels 13, 13, . . . , which will be described later. In the example of FIG. 6, the tubular main body 11a comprises an upper half and a lower half, which are fitted to each other.

Basically, the nucleic acid extracting apparatus 1 performs the extraction of the nucleic acid with the extracting steps illustrated in FIGS. 5A to 5G. Specifically, firstly, in the step illustrated in FIG. 5A, a sample liquid S containing the nucleic acid, which sample liquid S has been subjected to dissolution processing, is injected into the extracting cartridge 11, which is located above the corresponding waste liquid vessel 12. Thereafter, in the step illustrated in FIG. 5B, the pressurized air is introduced into the extracting cartridge 11, and the area within the extracting cartridge 11 is thus pressurized. As a result, the sample liquid S is caused to pass through the filter member 11b of the extracting cartridge 11 under pressure, and the nucleic acid contained in the sample liquid S is adsorbed to the filter member 11b. The liquid having passed through the filter member 11b is discharged into the corresponding waste liquid vessel 12.

Figure 5:
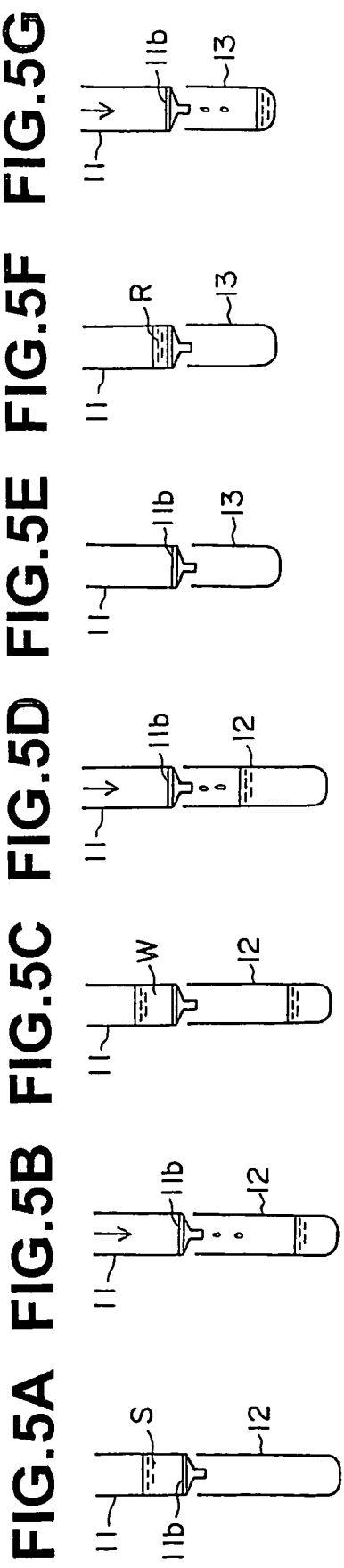
FIGS. 5A to 5G are flow diagrams showing an extracting operation.
Figure 6:
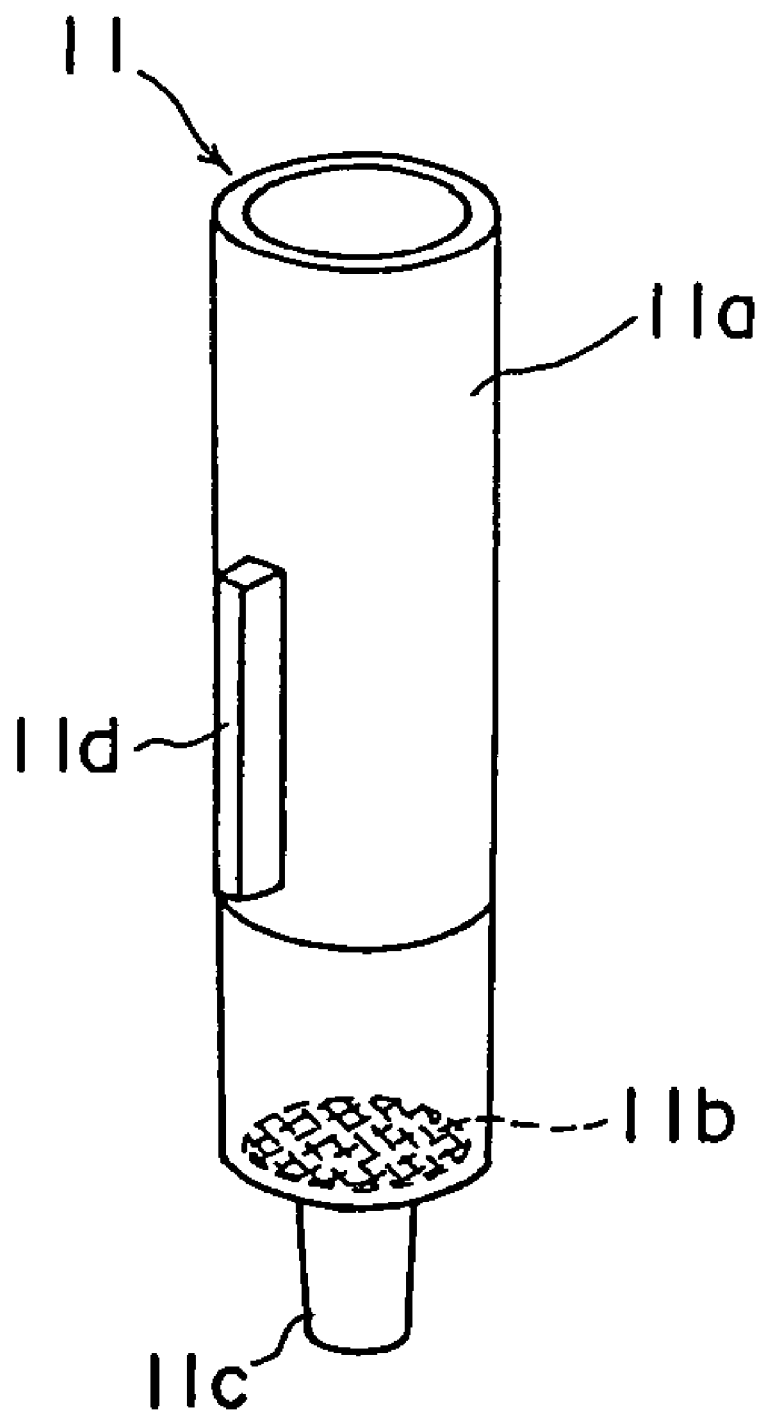
FIG. 6 is a perspective view showing an extracting cartridge.

Thereafter, in the step illustrated in FIG. 5C, a washing liquid W is automatically injected into the extracting cartridge 11. Also, in the step illustrated in FIG. 5D, the pressurized air is introduced into the extracting cartridge 11, and the area within the extracting cartridge 11 is thus pressurized. As a result, the washing liquid W is caused to pass through the filter member 11b of the extracting cartridge 11 under pressure. In this manner, impurities are removed by the washing liquid W from the extracting cartridge 11, while the nucleic acid is being kept in the state in which the nucleic acid has been adsorbed to the filter member 11b. The washing liquid W having passed through the filter member 11b is discharged into the waste liquid vessel 12. The step illustrated in FIG. 5C and the step illustrated in FIG. 5D may be iterated a plurality of times.

Thereafter, in the step illustrated in FIG. 5E, the waste liquid vessel 12, which is located under the extracting cartridge 11, is replaced by the recovery vessel 13. Also, in the step illustrated in FIG. 5F, a recovery liquid R is automatically injected into the extracting cartridge 11. Thereafter, in the step illustrated in FIG. 5G, the pressurized air is introduced into the extracting cartridge 11, and the area within the extracting cartridge 11 is thus pressurized. As a result, the recovery liquid R is caused to pass through the filter member 11b of the extracting cartridge 11 under pressure. In this manner, the binding force between the filter member 11b and the nucleic acid is weakened. The nucleic acid having been adsorbed to the filter member 11b of the extracting cartridge 11 is thus separated by the recovery liquid R from the filter member 11b. The recovery liquid R, which now contains the nucleic acid, is discharged from the extracting cartridge 11 and recovered into the recovery vessel 13.

The filter member (the nucleic acid-adsorbing porous film) 11b of the extracting cartridge 11 is constituted of the porous film capable of adsorbing the nucleic acid with an interaction other than interactions in which the ionic bond takes part. The filter member 11b is constituted such that the filter member 11b keeps the adsorption of the nucleic acid during the washing with the washing liquid, and such that the filter member 11b reduces the force of adsorption of the nucleic acid and releases the nucleic acid during the recovery of the nucleic acid with the recovery liquid. The filter member 11b should preferably be a porous film having a hydroxyl group as a hydrophilic group. In such cases, the filter member 11b may be a porous film constituted of a porous film material having the hydroxyl group by itself. Alternatively, the filter member 11b may be a porous film obtained from a process, in which the material for the formation of the porous film is subjected to treatment or coating, and the hydroxyl group is thereby introduced into the porous film material.

The material for the formation of the porous film may be an organic material or an inorganic material. For easiness of the processing, the material for the formation of the porous film should preferably be an organic material, such as an organic high-molecular weight material. Examples of the organic materials for the formation of the porous film include a nylon, a polysulfone, a polyethersulfone, a polycarbonate, a polyacrylate, an acrylate copolymer, a polyurethane, a polyamide, a polyvinyl chloride, a polyfluorocarbonate, a polytetrafluoroethylene, a polyvinylidene difluoride, a polyethylene-tetrafluoroethylene copolymer salt, a polybenzimidazole, a polyethylene-chlorotrifluoroethylene copolymer salt, a polyimide, a polyphenylene sulfide, cellulose, a cellulose mixed ester, a nitrocellulose, an acetylcellulose, a polyacrylonitrile, a polyacrylonitrile copolymer, a polypropylene, and a polyester.

Examples of the organic materials having the hydroxyl groups for the formation of the porous film include surface saponification products of acetylcelluloses described in, for example, U.S. patent laid-open No. 20030170664. The acetylcellulose may be monoacetylcellulose, diacetylcellulose, or triacetylcellulose. Among the above-enumerated acetylcelluloses, the triacetylcellulose is particularly preferable. In such cases, the quantity (the density) of the hydroxyl group in a solid phase surface is capable of being adjusted with the degree of the saponification processing (i.e., the saponification degree). In order for the efficiency with which the nucleic acid is separated to be enhanced, the quantity of the hydroxyl group should preferably be as large as possible (i.e., the density of the hydroxyl group should preferably be as high as possible). For example, in the cases of the acetylcellulose, such as the triacetylcellulose, the saponification degree should preferably be at least approximately 5%, and should more preferably be at least approximately 10%. Also, such that the surface area of the porous film may be set to be large, the porous film of the acetyl cellulose is subjected to the saponification processing. By the combination of the degree of the saponification processing (the saponification degree) of the porous film and the pore diameter of the porous film, the spatial quantity (the density) of the hydroxyl group is capable of being adjusted. In such cases, the porous film may be a porous film, in which a front surface side and a back surface side are symmetric with respect to each other. However, the porous film should preferably be a porous film, in which the front surface side and the back surface side are asymmetric with respect to each other.

Examples of the organic materials having the hydroxyl groups for the formation of the porous film also include a polyhydroxyethylacrylic acid, a polyhydroxyethylmethacrylic acid, a polyvinyl alcohol, a polyvinyl pyrrolidone, a polyacrylic acid, a polymethacrylic acid, a polyoxyethylene, an acetyl cellulose, and a mixture of acetylcelluloses having different acetyl values. A porous film of an organic material having a polysaccharide structure is capable of being used preferably. In particular, a porous film of an organic high-molecular weight material constituted of a mixture of acetylcelluloses having different acetyl values is capable of being used preferably. In such cases, the mixture of acetylcelluloses having different acetyl values should preferably be a mixture of triacetylcellulose and diacetylcellulose, a mixture of triacetylcellulose and monoacetylcellulose, a mixture of triacetylcellulose, diacetylcellulose, and monoacetylcellulose, or a mixture of diacetylcellulose and monoacetylcellulose.

Also, the filter member 11b may be a porous film constituted of an organic material, which is obtained from saponification processing of a mixture of acetylcelluloses having different acetyl values. In such cases, for example, the porous film should preferably be constituted of a saponification product of the mixture of triacetylcellulose and diacetylcellulose, the mixture of triacetylcellulose and monoacetylcellulose, the mixture of triacetylcellulose, diacetylcellulose, and monoacetylcellulose, or the mixture of diacetylcellulose and monoacetylcellulose. With the saponification processing, the acetylcellulose is brought into contact with a saponification processing liquid (e.g., sodium hydroxide). In such cases, the hydroxyl groups are introduced into the site of the acetylcellulose, which site has been brought into contact with the saponification processing liquid, and a regenerated cellulose is formed at the site of the acetylcellulose. In order for the efficiency with which the nucleic acid is separated is to be enhanced, the number of the hydroxyl groups introduced into the aforesaid site of the acetylcellulose should preferably be as large as possible. For example, the saponification degree should preferably be at least approximately 5%, and should more preferably be at least approximately 10%. In order for the saponification degree to be altered, the concentration of sodium hydroxide in the saponification processing may be altered.

Further, the filter member 11b may be a porous film constituted of a regenerated cellulose. The regenerated cellulose is obtained from a process, in which the surface of the solid of the acetylcellulose or the entire region of the solid of the acetylcellulose is converted into cellulose with the saponification processing. The characteristics, such as the crystal condition, of the regenerated cellulose are different from those of the natural cellulose.

Furthermore, the filter member 11b maybe a porous film constituted of an inorganic material having a hydrophilic group. In such cases, the porous film may be a porous film containing a silica compound, e.g. a glass filter. The porous film may also be a porous thin silica film described in, for example, Japanese Patent No. 3058342. The porous thin silica film is capable of being prepared with a process, wherein a spreading liquid of a cationic amphiphilic substance having capability of forming a bilayer membrane is spread on a base plate, a solvent is removed from the liquid film having been spread on the base plate, a thin bilayer membrane of the amphiphilic substance is thus prepared, the thus prepared thin bilayer membrane of the amphiphilic substance is then brought into contact with a solution containing a silica compound, and thereafter the thin bilayer membrane is extracted and removed.

The thickness of the porous film constituting the filter member 11b may fall within the range of 10 μm to 500 μm, and should preferably fall within the range of 50 μm to 250 μm. Also, the porous film constituting the filter member 11b may have a minimum pore diameter of at least 0.22 μm, and should preferably have a minimum pore diameter of at least 0.5 μm. Further, the ratio of the maximum pore diameter to the minimum pore diameter in the porous film constituting the filter member 11b may be at least 2, and should preferably be at least 5. Furthermore, the porosity of the porous film constituting the filter member 11b may fall within the range of 50% to 95%, and should preferably fall within the range of 65% to 80%.

Only one sheet of the filter member 11b may be used. Alternatively, a plurality of sheets of the filter members 11b, 11b, . . . may be utilized. In cases where the plurality of sheets of the filter members 11b, 11b, . . . are utilized, the plurality of the filter members 11b, 11b, . . . may be of an identical type. Alternatively, the plurality of the filter members 11b, 11b, . . . may be of different types. Also, the plurality of the filter members 11b, 11b, . . . may be constituted of a combination of a filter member 11b of an inorganic material and a filter member 11b of an organic material. For example, the plurality of the filter members 11b, 11b, . . . may be constituted of a combination of a glass filter and a porous film of a regenerated cellulose. Alternatively, the plurality of the filter members 11b, 11b, . . . may be constituted of a combination of a filter member 11b of an inorganic material and a nucleic acid-nonadsorbing porous film of an organic material. For example, the plurality of the filter members 11b, 11b, . . . may be constituted of a combination of a glass filter and a porous film of a nylon or a polysulfone.

The aforesaid sample liquid S containing the nucleic acid is prepared with a process, wherein a liquid in which the nucleic acid has been dispersed is prepared with the dissolution processing of a sample, which contains a cell or a virus, and a water-soluble organic solvent is added to the liquid in which the nucleic acid has been dispersed. For example, in the cases of diagnostic fields, the sample liquid S containing the nucleic acid may be a liquid having been prepared from an organism material, such as a humor having been taken as a sample (e.g., whole blood, blood plasma, blood serum, urine, feces, semen, or saliva); a plant (or part of a plant); an animal (or part of an animal). Also, the sample liquid S containing the nucleic acid may be a liquid having been prepared from a dissolution product or a homogenate of one of the above-enumerated organism materials. With the dissolution processing, a sample is processed with an aqueous solution containing a reagent for dissolving a cell membrane and a nuclear membrane and solubilizing the nucleic acid. (The reagent is a solution containing, for example, a guanidine salt, a surface active agent, and a proteolytic enzyme.) For example, in cases where the sample is whole blood, red blood corpuscles and various proteins are decomposed and converted into low-molecular weight substances in order for nonspecific adsorption to the filter member 11b and clogging of the filter member 11b to be prevented from occurring, and dissolution of white blood corpuscles and a nuclear membrane is performed such that the nucleic acid to be extracted may be solubilized. Examples of the water-soluble organic solvents include ethanol, isopropanol, and propanol. Among the above-enumerated water-soluble organic solvents, ethanol is preferable. The concentration of the water-soluble organic solvent should preferably fall within the range of 5% by weight to 90% by weight, and should more preferably fall within the range of 20% by weight to 60% by weight. The concentration of ethanol added should particularly preferably be as high as possible, provided that an agglomerate does not occur.

The washing liquid W has the functions of washing off impurities contained in the sample liquid, which impurities have clung to the filter member 11b together with the nucleic acid. The washing liquid W has a composition such that the washing liquid W does not cause the nucleic acid to be separated from the filter member 11b and causes the impurities to be separated from the filter member 11b. The washing liquid W is constituted of a solution containing a principal agent and a buffer agent. When necessary, the solution constituting the washing liquid W may also contain a surface active agent. Examples of the principal agents include aqueous solutions of methanol, ethanol, isopropanol, n-isopropanol, butanol, and acetone. The concentration of the aqueous solution acting as the principal agent may fall within the range of approximately 10% by weight to approximately 100% by weight. The concentration of the aqueous solution acting as the principal agent should preferably fall within the range of approximately 20% by weight to approximately 100% by weight, and should more preferably fall within the range of approximately 40% by weight to approximately 80% by weight.

The recovery liquid R should preferably have a low salt concentration. In particular, the recovery liquid R should preferably be constituted of a solution having a salt concentration of at most 0.5M. For example, purified distilled water, a TE buffer, or the like, may be used as the recovery liquid R. The pH value of the recovery liquid R should preferably fall within the range of pH2 to pH11, and should more preferably fall within the range of pH5 to pH9.

As illustrated in FIG. 1 and FIG. 2, the nucleic acid extracting apparatus 1 comprises a loading mechanism 3, a pressurized air supplying mechanism 4, and a liquid injecting mechanism 5, which are located on an apparatus main body 2. The loading mechanism 3 holds a plurality of extracting cartridges 11, 11, . . . , the plurality of the waste liquid vessels 12, 12, . . . , and the plurality of the recovery vessels 13, 13, . . . The pressurized air supplying mechanism 4 introduces the pressurized air into each of the extracting cartridges 11, 11, . . . The liquid injecting mechanism 5 injects the washing liquid W into each of the extracting cartridges 11, 11, . . . The liquid injecting mechanism 5 also injects the recovery liquid R into each of the extracting cartridges 11, 11, . . . . The loading mechanism 3, the pressurized air supplying mechanism 4, and the liquid injecting mechanism 5 will hereinbelow be described in more detail.

<Loading Mechanism>

The loading mechanism 3 comprises a loading base 21, which is located on a front lower part of the apparatus main body 2. A rack 6, which holds the plurality of the extracting cartridges 11, 11, . . . , the plurality of the waste liquid vessels 12, 12, . . . , and the plurality of the recovery vessels 13, 13, . . . , is located on the loading base 21. As illustrated also in FIG. 3, the rack 6 comprises a stand 61, a cartridge holder 62, and a vessel holder 63.

The stand 61 is provided with pillar-shaped sections 61*a*, 61*a*, which are spaced apart from each other. The pillar-shaped sections 61*a*, 61*a* of the stand 61 hold the cartridge holder 62 such that the cartridge holder 62 is capable of moving vertically. The stand 61 is also provided with a bottom plate 61*b*, on which the pillar-shaped sections 61*a*, 61*a* are supported. The region of the bottom plate 61*b*, which region is located between the pillar-shaped sections 61*a*, 61*a*, holds the vessel holder 63 such that the vessel holder 63 is capable of undergoing forward and backward movements.

The cartridge holder 62 has a two-part structure, which is formed with joining of a front plate material and a rear plate material. The cartridge holder 62 comprises a holding section 62*a*, which extends horizontally, and support legs 62*b*, 62*b*, which extend vertically from opposite end regions of the holding section 62*a*. Each of the support legs 62*b*, 62*b* of the cartridge holder 62 is inserted for vertical movement into one of vertically extending sliding grooves 61*c*, 61*c* of the pillar-shaped sections 61*a*, 61*a* of the stand 61. The support legs 62*b*, 62*b* of the cartridge holder 62 are urged upwardly by urging members (not shown), which are incorporated in the stand 61. The holding section 62*a* of the cartridge holder 62 has a plurality of holding holes 62*c*, 62*c*, . . . , which stand side by side with one another. Each of the extracting cartridges 11, 11, . . . is inserted from above into one of the holding holes 62*c*, 62*c*, . . . of the cartridge holder 62, and lower ends of the protrusions 11*d*, 11*d* (illustrated in FIG. 6), which are formed on the opposite sides of the side wall of the tubular main body 11*a* of the extracting cartridge 11, are engaged with engagement members (not shown) located in the cartridge holder 62 and are held by the engagement members. The engagement members located in the cartridge holder 62 are capable of being moved. At the time at which the engagement members located in the cartridge holder 62 are moved, the engagement members release the engagement with the protrusions 11*d*, 11*d* of each of the extracting cartridges 11, 11, . . . As a result, all of the extracting cartridges 11, 11, . . . are simultaneously allowed to fall down from the cartridge holder 62 and are thus scrapped.

The cartridge holder 62 also has pin receiving holes 62*d*, 62*d*, which are formed at opposite areas of the top surface of the cartridge holder 62. In the state in which the extracting cartridges 11, 11, . . . are to be used for the extraction of the nucleic acid, each of bottom ends 49*a*, 49*a* of push pins 49, 49 (illustrated in FIG. 1), which act as the position adjusting means as will be described later, engages with one of the pin receiving holes 62*d*, 62*d* of the cartridge holder 62 and pushes down the cartridge holder 62. As illustrated in FIG. 3, in the state in which the cartridge holder 62 is located at the raised position, the discharging bottom end 11*c* of each of the extracting cartridges 11, 11, . . . having been held by the cartridge holder 62 is located at the position more upward than the waste liquid vessels 12, 12, . . . and the recovery vessels 13, 13, . . . having been set on the vessel holder 63. As illustrated in FIG. 4, in the state in which the cartridge holder 62 has been pushed down by the push pins 49, 49 acting as the position adjusting means, the discharging bottom end 11*c* of each of the extracting cartridges 11, 11, . . . having been held by the cartridge holder 62 is inserted by a predetermined length into the corresponding one of the waste liquid vessels 12, 12, . . . , which have been set on the vessel holder 63, or the corresponding one of the recovery vessels 13, 13, . . . , which have been set on the vessel holder 63 so that scattering from the discharging bottom end 11*c* of each of the extracting cartridges 11 can be prevented.

The vessel holder 63 is provided with a plurality of waste liquid vessel holding holes 63*a*, 63*a*, . . . , which stand side by side in a row extending horizontally, and a plurality of recovery vessel holding holes 63*b*, 63*b*, . . . , which stand side by side in a row extending horizontally. The row of the waste liquid vessel holding holes 63*a*, 63*a*, . . . and the row of the recovery vessel holding holes 63*b*, 63*b*, . . . are parallel with each other. The plurality of the waste liquid vessels 12, 12, . . . are held in a row within the waste liquid vessel holding holes 63*a*, 63*a*, . . . , respectively, which are located on the rear side. Also, the plurality of the recovery vessels 13, 13, . . . are held in a row within the recovery vessel holding holes 63*b*, 63*b*, . . . , respectively, which are located on the front side. The waste liquid vessel holding holes 63*a*, 63*a*, . . . are located at the pitches identical with the pitches of the holding holes 62*c*, 62*c*, . . . of the cartridge holder 62 and at the positions corresponding to the positions of the holding holes 62*c*, 62*c*, . . . of the cartridge holder 62. Also, the recovery vessel holding holes 63*b*, 63*b*, . . . are located at the pitches identical with the pitches of the holding holes 62*c*, 62*c*, . . . of the cartridge holder 62 and at the positions corresponding to the positions of the holding holes 62*c*, 62*c*, . . . of the cartridge holder 62. The vessel holder 63 is thus set such that each of the waste liquid vessels 12, 12, . . . or each of the recovery vessels 13, 13, . . . is located under one of the extracting cartridges 11, 11, . . . having been held by the cartridge holder 62. Such that the waste liquid vessels 12, 12, . . . and the recovery vessels 13, 13, . . . may be discriminated from each other, the sizes, the shapes, or the like, of the waste liquid vessels 12, 12, . . . should preferably be different from the sizes, the shapes, or the like, of the recovery vessels 13, 13, . . .

The vessel holder 63 is urged toward the front side by urging members (not shown), which are incorporated in the stand 61. The movements (i.e., the forward and backward movements) of the vessel holder 63 for the vessel changeover are performed with an actuating member 31 (illustrated in FIG. 2) of the loading base 21. Specifically, the actuating member 31 of the loading base 21 passes through an opening formed in the bottom plate 61*b* of the stand 61 and engages with an engagement hole (not shown) of the bottom part of the vessel holder 63. Also, the actuating member 31 is moved by a vessel changeover motor (a DC motor) 32 in order to move the vessel holder 63 backwardly. The recovery vessels 13, 13, . . . are thus located at the position under the cartridge holder 62. In the state in which the actuating member 31 is not operated, the vessel holder 63 is urged toward the front side by the urging members (not shown), which are incorporated in the stand 61, such that the waste liquid vessels 12, 12, . . . are located at the position under the cartridge holder 62. The vessel changeover motor 32 is controlled in accordance with results of detection made by position sensors 33*a* and 33*b* (illustrated in FIG. 2).

The waste liquid vessel holding holes 63*a*, 63*a*, . . . and the recovery vessel holding holes 63*b*, 63*b*, . . . are constituted of bottomed holes. Therefore, in cases where a liquid drops into the waste liquid vessel holding holes 63a, 63a, . . . or the recovery vessel holding holes 63b, 63b, . . . in the state in which the waste liquid vessels 12, 12, . . . have not been set in the waste liquid vessel holding holes 63a, 63a, . . . or in which the recovery vessels 13, 13, . . . have not been set in the recovery vessel holding holes 63b, 63b, . . . , the problems are capable of being prevented from occurring in that the liquid flows out to the exterior and contaminates the exterior equipment.

<Pressurized Air Supplying Mechanism>

As illustrated in FIG. 1 and FIG. 2, the pressurized air supplying mechanism 4 comprises a pressurizing head 40, which is capable of moving vertically with respect to the rack 6 of the loading mechanism 3. The pressurized air supplying mechanism 4 also comprises a plurality of (in this example, eight) air nozzles 41, 41, . . . , which are fitted to the pressurizing head 40 and located in a row. The pressurized air supplying mechanism 4 further comprises an air pump 43 for producing the pressurized air. The pressurized air supplying mechanism 4 still further comprises a relief valve 44 (illustrated in FIG. 2). The pressurized air supplying mechanism 4 also comprises a plurality of on-off valves 45, 45, . . . , which are connected respectively to the air nozzles 41, 41, . . . and which are turned on and off independently. The pressurized air supplying mechanism 4 further comprises a plurality of pressure sensors 46, 46, . . . , which are respectively associated with the air nozzles 41, 41, . . . The pressurized air supplying mechanism 4 successively supplies the pressurized air into the extracting cartridges 11, 11, . . .

The pressurizing head 40 is held for vertical movement by guide rods 24, 24, which extend vertically between an intermediate frame 22 and a top frame 23 of the apparatus main body 2. Also, a ball nut 40a secured to the pressurizing head 40 is engaged with a ball screw 25, which extends vertically between the intermediate frame 22 and the top frame 23 of the apparatus main body 2. The ball screw 25 is rotated by a vertical movement motor (a pulse motor) 47 (illustrated in FIG. 2) via a timing belt and a pulley. In accordance with the rotation of the ball screw 25, the pressurizing head 40 is moved vertically. The pressurizing head 40 is moved by being controlled in accordance with the results of detection of photo sensors 48a, 48b, and 48c (illustrated in FIG. 2). The pressurizing head 40 is also provided with the push pins 49, 49, which are located on opposite sides of the pressurizing head 40 and act as the position adjusting means. Each of the push pins 49, 49 is urged by a spring 49b downwardly and is capable of moving vertically. Each of the bottom ends 49a, 49a of the push pins 49, 49 engages with one of the pin receiving holes 62d, 62d, which are formed in the top surface of the cartridge holder 62. The push pins 49, 49 thus adjust the position of the cartridge holder 62 and push down the cartridge holder 62.

The push pins 49, 49 of the pressurizing head 40 are located so as to push the front side positions on the cartridge holder 62, such that the push pins 49, 49 do not interfere with horizontal movements of a washing liquid injecting nozzle 51w and a recovery liquid injecting nozzle 51r, which will be described later, in the state in which the push pins 49, 49 push down the cartridge holder 62.

The air nozzles 41, 41, . . . are fitted for vertical movement to the pressurizing head 40 and are urged downwardly. Also, a sheet-shaped sealing material 42 is located under the air nozzles 41, 41, . . . The sealing material 42 has a plurality of communication holes 42a, 42a, . . . (illustrated in FIG. 2), each of which corresponds to one of the air nozzles 41, 41, . . . At the time at which the pressurizing head 40 is moved down, the bottom end of each of the air nozzles 41, 41, . . . pushes the sealing material 42 against the top end opening of the corresponding extracting cartridge 11 having been set on the cartridge holder 62 and thus closes the top end opening of the corresponding extracting cartridge 11. Each of the air nozzles 41, 41, . . . is thus capable of supply the pressurized air through the communication hole 42a into the extracting cartridge 11.

In cases where the pressurized air contained in the pressurized air path between the air pump 43 and the on-off valves 45, 45, . . . is to be discharged from the pressurized air path, the relief valve 44 is opened to the ambient atmosphere. The pressurized air circuit is constituted such that each of the on-off valves 45, 45, . . . is turned on selectively in order to introduce the pressurized air from the air pump 43 via the corresponding air nozzle 41 into the corresponding extracting cartridge 11. Each of the pressure sensors 46, 46, . . . is associated with one of the air nozzles 41, 41, . . . and detects the internal pressure of the corresponding extracting cartridge 11. At the time at which the detected internal pressure of the extracting cartridge 11 becomes a predetermined pressure range (for example, 50-200 kPa, and preferably, 80-120 kPa), the corresponding on-off valve 45 is turned off, and the supply of the pressurized air into the extracting cartridge 11 is ceased. Also, in cases where the detected internal pressure of the extracting cartridge 11 becomes lower than the predetermined value, it is judged that a liquid discharging operation for the extracting cartridge 11 has been completed.

In the descriptions of the embodiments, the air pump is a diaphragm pump. However, other kinds of pumps such as a plunger pump and a syring pump, which can function as a pressurized air source, may be used as the air pump.

<Liquid Injecting Mechanism>

The liquid injecting mechanism 5 comprises the washing liquid injecting nozzle 51w and the recovery liquid injecting nozzle 51r, which are secured to a nozzle moving base 50 capable of moving horizontally. The liquid injecting mechanism 5 also comprises a washing liquid supplying pump 52w (illustrated in FIG. 2) for supplying the washing liquid W, which has been accommodated in a washing liquid bottle 56w, into the washing liquid injecting nozzle 51w. The liquid injecting mechanism 5 further comprises a recovery liquid supplying pump 52r (illustrated in FIG. 2) for supplying the recovery liquid R, which has been accommodated in a recovery liquid bottle 56r, into the recovery liquid injecting nozzle 51r. The liquid injecting mechanism 5 still further comprises a waste liquid bottle 57, which is located on the loading base 21.

The nozzle moving base 50 is held for horizontal movement by a guide rail 27, which extends horizontally and is secured to a vertical wall 26 of the apparatus main body 2. The horizontal movement of the nozzle moving base 50 is ceased successively above the extracting cartridges 11, 11, . . . by a nozzle moving motor (not shown) constituted of a pulse motor. In a state of restoration of the nozzle moving base 50, the nozzle moving base 50 is stopped at the position above the waste liquid bottle 57. An end of the washing liquid injecting nozzle 51w and an end of the recovery liquid injecting nozzle 51r are bent downwardly. The washing liquid injecting nozzle 51w is connected to the washing liquid supplying pump 52w via a changeover valve 55w (illustrated in FIG. 2). The washing liquid supplying pump 52w is connected to the washing liquid bottle 56w via the changeover valve 55w. Also, the recovery liquid injecting nozzle 51r is connected to the recovery liquid supplying pump 52r via a changeover valve 55r.

The recovery liquid supplying pump 52r is connected to the recovery liquid bottle 56r via the changeover valve 55r. The washing liquid bottle 56w and the recovery liquid bottle 56r are fitted to a side of the apparatus main body 2. Each of the washing liquid supplying pump 52w and the recovery liquid supplying pump 52r is constituted of a syringe pump. A piston member of the washing liquid supplying pump 52w is actuated by a pump motor 53w (illustrated in FIG. 2), which is constituted of a pulse motor, and in accordance with a result of a position detection made by a sensor 54w in order to inject a predetermined quantity of the washing liquid W. Also, a piston member of the recovery liquid supplying pump 52r is actuated by a pump motor 53r (illustrated in FIG. 2), which is constituted of a pulse motor, and in accordance with a result of a position detection made by a sensor 54r in order to inject a predetermined quantity of the recovery liquid R.

Specifically, in cases where the washing liquid W is to be injected, the changeover valve 55w is changed over to the side for the washing liquid bottle 56w. Also, the pump motor 53w is actuated in order to retreat the piston member of the washing liquid supplying pump 52w, and the washing liquid W is thus sucked into the washing liquid supplying pump 52w. Thereafter, the changeover valve 55w is changed over to the side for the washing liquid injecting nozzle 51w. Also, the pump motor 53w is actuated in order to advance the piston member of the washing liquid supplying pump 52w, and the washing liquid W is thus discharged from the washing liquid injecting nozzle 51w into the waste liquid bottle 57 until air contained in the washing liquid path has been discharged. The actuation of the washing liquid supplying pump 52w is then ceased. Thereafter, the washing liquid injecting nozzle 51w is moved to the position above one of the extracting cartridges 11, 11, . . . The actuation quantity of the washing liquid supplying pump 52w is then controlled, and the predetermined quantity of the washing liquid W is injected into the extracting cartridge 11.

In cases where the recovery liquid R is to be injected, the changeover valve 55r is changed over to the side for the recovery liquid bottle 56r. Also, the pump motor 53r is actuated in order to retreat the piston member of the recovery liquid supplying pump 52r, and the recovery liquid R is thus sucked into the recovery liquid supplying pump 52r. Thereafter, the changeover valve 55r is changed over to the side for the recovery liquid injecting nozzle 51r. Also, the pump motor 53r is actuated in order to advance the piston member of the recovery liquid supplying pump 52r, and the recovery liquid R is thus discharged from the recovery liquid injecting nozzle 51r into the waste liquid bottle 57 until air contained in the recovery liquid path has been discharged. The actuation of the recovery liquid supplying pump 52r is then ceased. Thereafter, the recovery liquid injecting nozzle 51r is moved to the position above one of the extracting cartridges 11, 11, . . . The actuation quantity of the recovery liquid supplying pump 52r is then controlled, and the predetermined quantity of the recovery liquid R is injected into the extracting cartridge 11.

The washing liquid bottle 56w comprises a vessel main body 56wb and a cap 56wu. A thin pipe-shaped suction tube 58w is fitted into the cap 56wu so as to extend within the vessel main body 56wb, and a bottom end of the suction tube 58w is open at a position in the vicinity of a bottom of the vessel main body 56wb. In accordance with the operation of the washing liquid supplying pump 52w, the washing liquid W is sucked from the vessel main body 56wb through the suction tube 58w. Further, the cap 56wu is provided with a pipe or an opening (not shown), through which air is introduced into the vessel main body 56wb in accordance with the suction of the washing liquid W from the vessel main body 56wb.

The recovery liquid bottle 56r comprises a vessel main body 56rb and a cap 56ru. A thin pipe-shaped suction tube 58r is fitted into the cap 56ru so as to extend within the vessel main body 56rb, and a bottom end of the suction tube 58r is open at a position in the vicinity of a bottom of the vessel main body 56rb. In accordance with the operation of the recovery liquid supplying pump 52r, the recovery liquid R is sucked from the vessel main body 56rb through the suction tube 58r. Further, the cap 56ru is provided with a pipe or an opening (not shown), through which air is introduced into the vessel main body 56rb in accordance with the suction of the recovery liquid R from the vessel main body 56rb.

The quantity of the washing liquid W used is larger than the quantity of the recovery liquid R used. Therefore, the vessel main body 56wb of the washing liquid bottle 56w has a height larger than the height of the vessel main body 56rb of the recovery liquid bottle 56r. Also, the suction tube 58w for the washing liquid W has a length larger than the length of the suction tube 58r for the recovery liquid R. The diameter of a threaded mouth section of the vessel main body 56wb of the washing liquid bottle 56w is identical with the diameter of a threaded mouth section of the vessel main body 56rb of the recovery liquid bottle 56r.

The washing liquid bottle 56w is fitted to the apparatus main body 2 in the manner described below. Specifically, the cap 56wu, to which the suction tube 58w has been secured, is fitted by a fixture 28 to the intermediate frame 22 of the apparatus main body 2. Also, the vessel main body 56wb is engaged by threads with the cap 56wu from below the cap 56wu, while the suction tube 58w is being inserted into the mouth section of the vessel main body 56wb. Since the washing liquid bottle 56w is thus fitted to the apparatus main body 2, the problems are capable of being prevented from occurring in that, in cases where the cap 56wu provided with the suction tube 58w is disengaged from the vessel main body 56wb at the time of replenishment of the washing liquid W into the vessel main body 56wb and is placed upon a table, or the like, a foreign substance clings to the end of the suction tube 58w having been fitted to the cap 56wu and mixes into the washing liquid W.

Also, the recovery liquid bottle 56r is fitted to the apparatus main body 2 in the manner described below. Specifically, the cap 56ru, to which the suction tube 58r has been secured, is fitted by a fixture 28 to the intermediate frame 22 of the apparatus main body 2. Also, the vessel main body 56rb is engaged by threads with the cap 56ru from below the cap 56ru, while the suction tube 58r is being inserted into the mouth section of the vessel main body 56rb. Since the recovery liquid bottle 56r is thus fitted to the apparatus main body 2, the problems are capable of being prevented from occurring in that, in cases where the cap 56ru provided with the suction tube 58r is disengaged from the vessel main body 56rb at the time of replenishment of the recovery liquid R into the vessel main body 56rb and is placed upon a table, or the like, a foreign substance clings to the end of the suction tube 58r having been fitted to the cap 56ru and mixes into the recovery liquid R.

In particular, as for the washing liquid bottle 56w having the large vessel height, a distance H between the bottom end of the suction tube 58w at the time of the disengagement of the 56wb from the cap 56wu and the table surface, which is located below the bottom end of the suction tube 58w and which supports the apparatus main body 2, is set to be larger than the height h of the vessel main body 56wb. Specifically, it is necessary that the height position at which the cap 56*wu* is located with the fixture 28 be set at a position higher than the table surface by at least approximately two times the height h of the vessel main body 56*wb*. In cases where the washing liquid bottle 56*w* is thus set, replacement of the vessel main body 56*wb* and the liquid replenishing operation are capable of being performed easily, while the cap 56*wu* provided with the suction tube 58*w* is being secured. The recovery liquid bottle 56*r* is set basically in the same manner as that described above.

The loading mechanism 3, the pressurized air supplying mechanism 4, and the liquid injecting mechanism 5 described above are controlled in accordance with an input operation performed from an operation panel 7 located at the top of the apparatus main body 2 and in accordance with a program incorporated within a control unit (not shown).

The extracting operation performed with the nucleic acid extracting apparatus 1 described above will hereinbelow be described in detail.

Firstly, the extracting cartridges 11, 11, ... are set in the cartridge holder 62 of the rack 6 of the loading mechanism 3. Also, the waste liquid vessels 12, 12, ... and the recovery vessels 13, 13, ... are set in the vessel holder 63 of the rack 6 of the loading mechanism 3. The rack 6 is then located on the loading base 21 of the apparatus main body 2. Thereafter, the sample liquid S, which has been subjected to the dissolution processing, is introduced with a pipette, or the like, successively into each of the extracting cartridges 11, 11, ... Alternatively, before the rack 6 is loaded on the nucleic acid extracting apparatus 1, the sample liquid S may be introduced into each of the extracting cartridges 11, 11, ... having been set in the rack 6. As another alternative, before the extracting cartridges 11, 11, ... are set in the rack 6, the sample liquid S may be introduced into each of the extracting cartridges 11, 11, ...

Thereafter, the nucleic acid extracting apparatus 1 is actuated with an operation from the operation panel 7. The pressurizing head 40 of the pressurized air supplying mechanism 4 is moved downwardly by the vertical movement motor 47 of the pressurized air supplying mechanism 4, and the bottom ends 49*a*, 49*a* of the push pins 49, 49 engage with the pin receiving holes 62*d*, 62*d* of the cartridge holder 62. The push pins 49, 49 thus push down the cartridge holder 62 and adjust the position of the cartridge holder 62. Also, as illustrated in FIG. 4, a scattering prevention means, wherein the push pins 49, 49 cause the discharging bottom end 11*c* of each of the extracting cartridges 11, 11, ... to be inserted by the predetermined length into the corresponding waste liquid vessel 12, is provided such that the liquid discharged from the extracting cartridge 11 may not leak to the exterior due to scattering, or the like, and may not cause the problems with regard to contamination to occur. The pressurizing head 40 is moved downwardly even further. As a result, the bottom end of each of the air nozzles 41, 41, ... pushes the sealing material 42 against the top end opening of the corresponding extracting cartridge 11 and thus closes the top end opening of the corresponding extracting cartridge 11. Since the push pins 49, 49 adjust the position of the cartridge holder 62, each of the air nozzles 41, 41, ... is capable of accurately coming into close contact with the top end opening of the corresponding extracting cartridge 11 and is thus capable of reliably closing the top end opening of the corresponding extracting cartridge 11.

Thereafter, the operation for supplying the pressurized air is performed. Specifically, the air pump 43 is actuated in the state in which all of the on-off valves 45, 45, ... are turned off. Also, firstly, a first on-off valve 45 is turned on. As a result, the pressurized air is supplied from the air pump 43 through a first air nozzle 41 into a first extracting cartridge 11. At the time at which the pressure sensor 46 associated with the first air nozzle 41 detects that the pressure within the. first extracting cartridge 11 has reached the predetermined pressure, the first on-off valve 45 is turned off. A second on-off valve 45 is then turned on, and the pressurized air is supplied from the air pump 43 through a second air nozzle 41 into a second extracting cartridge 11. The operation described above is iterated successively for the extracting cartridges 11, 11, ..., and the areas within all of the extracting cartridges 11, 11, ... are thus pressurized. When the sample liquid S is thus subjected to the pressure, the sample liquid S is caused to pass through the filter member 11*b* of each of the extracting cartridges 11, 11, ..., and the nucleic acid contained in the sample liquid S is adsorbed to the filter member 11*b*. Other liquid constituents of the sample liquid S are discharged through the discharging bottom end 11*c* of the extracting cartridge 11 into the corresponding waste liquid vessel 12. At the time at which all sample liquid S having been introduced into the extracting cartridge 11 has passed through the filter member 11*b* of the extracting cartridge 11, the pressure within the extracting cartridge 11 decreases to a level lower than a liquid discharging completion pressure. When the pressure sensors 46, 46, ... detect that the extracting operation has been finished for all of the extracting cartridges 11, 11, ..., the pressurizing head 40 is moved upwardly.

Thereafter, the washing processing is performed. Specifically, after the supply of the pressurized air, the pressurizing head 40 is moved upwardly as described above, and the air nozzles 41, 41, ... move away from the extracting cartridges 11, 11, ... When the pressurizing head 40 has been moved up to a height position at which the pressurizing head 40 allows the horizontal movement of the nozzle moving base 50, the upward movement of the pressurizing head 40 is ceased. The washing processing is performed in the state illustrated in FIG. 4, in which the push pins 49, 49 push down the cartridge holder 62 and in which the discharging bottom end 11*c* of each of the extracting cartridges 11, 11, ... has been inserted into the corresponding waste liquid vessel 12. More specifically, the nozzle moving base 50 is moved horizontally, and the washing liquid injecting nozzle 51*w* is stopped at the position above the first extracting cartridge 11. In this state, a predetermined quantity of the washing liquid W is injected from the washing liquid injecting nozzle 51*w* into the first extracting cartridge 11. The nozzle moving base 50 is then moved successively to the positions above the other extracting cartridges 11, 11, ..., and the injection of the washing liquid W from the washing liquid injecting nozzle 51*w* into the extracting cartridges 11, 11, ... is performed successively. When the injection of the washing liquid W has been finished for all of the extracting cartridges 11, 11, ..., the pressurizing head 40 is moved downwardly, and the bottom end of each of the air nozzles 41, 41, ... pushes the sealing material 42 against the top end opening of the corresponding extracting cartridge 11 and thus closes the top end opening of the corresponding extracting cartridge 11. Thereafter, in the same manner as that described above, the on-off valves 45, 45, ... are turned on successively, and the pressurized air is supplied into the extracting cartridges 11, 11, ... When the washing liquid W is thus subjected to the pressure, the washing liquid W is caused to pass through the filter member 11*b* of each of the extracting cartridges 11, 11, ..., and the impurities other than the nucleic acid are washed off by the washing liquid W. The washing liquid W having passed through the filter member 11*b* is discharged through the discharging bottom end 11*c* of the extracting cartridge 11 into the corresponding waste liquid vessel 12. At the time at which all washing liquid W contained in all of the extracting cartridges 11, 11, . . . has passed through the filter members 11b, 11b, . . . of the extracting cartridges 11, 11, . . . and has thus been discharged from the extracting cartridges 11, 11, . . . , the pressurizing head 40 is moved upwardly to the initial position. In cases where the washing processing is to be performed a plurality of times, the operation described above is iterated.

Thereafter, the recovery processing is performed. Specifically, firstly, in accordance with the upward movement of the pressurizing head 40 performed after the washing processing, the push pins 49, 49 move upwardly, and the cartridge holder 62 of the rack 6 also moves upwardly. The discharging bottom end 11c of each of the extracting cartridges 11, 11, . . . is thus moved upwardly from the corresponding waste liquid vessel 12. Thereafter, the actuating member 31 of the loading mechanism 3 is operated in order to retreat the vessel holder 63. The recovery vessels 13, 13, . . . are thus located under the extracting cartridges 11, 11, . . . The vessel changeover is performed in this manner.

Thereafter, the pressurizing head 40 is moved downwardly, and the bottom ends 49a, 49a of the push pins 49, 49 engage with the pin receiving holes 62d, 62d of the cartridge holder 62. The push pins 49, 49 thus push down the cartridge holder 62 and keep the state in which the discharging bottom end 11c of each of the extracting cartridges 11, 11, . . . has been inserted by the predetermined length into the corresponding recovery vessel 13. Also, the nozzle moving base 50 is moved horizontally, and the recovery liquid injecting nozzle 51r is stopped at the position above the first extracting cartridge 11. In this state, a predetermined quantity of the recovery liquid R is injected from the recovery liquid injecting nozzle 51r into the first extracting cartridge 11. The nozzle moving base 50 is then moved successively to the positions above the other extracting cartridges 11, 11, . . . , and the injection of the recovery liquid R from the recovery liquid injecting nozzle 51r into the extracting cartridges 11, 11, . . . is performed successively. When the injection of the recovery liquid R has been finished for all of the extracting cartridges 11, 11, . . . , the pressurizing head 40 is moved downwardly even further in the same manner as that described above, and the bottom end of each of the air nozzles 41, 41, . . . pushes the sealing material 42 against the top end opening of the corresponding extracting cartridge 11 and thus closes the top end opening of the corresponding extracting cartridge 11. Thereafter, the on-off valves 45, 45, . . . are turned on successively, and the pressurized air is supplied into the extracting cartridges 11, 11, . . . When the recovery liquid R is thus subjected to the pressure, the recovery liquid R is caused to pass through the filter member 11b of each of the extracting cartridges 11, 11, . . . , and the nucleic acid having been adsorbed to the filter member 11b is separated by the recovery liquid R from the filter member 11b. The nucleic acid having thus been separated from the filter member 11b is discharged together with the recovery liquid R through the discharging bottom end 11c of the extracting cartridge 11 into the corresponding recovery vessel 13. At the time at which all recovery liquid R contained in all of the extracting cartridges 11, 11, . . . has thus been discharged from the extracting cartridges 11, 11, . . . , the pressurizing head 40 is moved upwardly. At this stage, the series of the operations are finished.

The rack 6, for which the extracting operation has been finished, is unloaded from the loading base 21. Also, the extracting cartridges 11, 11, . . . and the waste liquid vessels 12, 12, . . . are taken out respectively from the cartridge holder 62 and the vessel holder 63 and scrapped. The recovery vessels 13, 13, . . . are taken out from the vessel holder 63. When necessary, the recovery vessels 13, 13, . . . are closed with covers. Thereafter, the recovery vessels 13, 13, . . . are subjected to next nucleic acid analyzing processing, or the like.

As described above, with the overlapping quantity between the discharging bottom end 11c of each of the extracting cartridges 11, 11, . . . and the corresponding waste liquid vessel 12 or the corresponding recovery vessel 13, the scattering of the discharged liquid and the problems with regard to contamination are prevented from occurring. In cases where the overlapping quantity described above is large, large effects of preventing the scattering of the discharged liquid are capable of being obtained. However, if the overlapping quantity described above is markedly large, the necessary movement distances of the cartridge holder 62 and the pressurizing head 40 will become long, and the nucleic acid extracting apparatus will not be capable of being kept small in size.

In the embodiment described above, when the pressurized air is supplied to the extracting cartridge 11 and the sample liquid S, the washing liquid W and the recovery liquid R are discharged to the waste liquid vessel 12 or the recovery vessel 13, the discharging bottom end 11c is of the extracting cartridge 11 is inserted to the waste liquid vessel 12 or the recovery vessel 13 by a predetermined length as a means for preventing scattering of the discharged liquid from the discharging bottom end 11c of the extracting cartridge 11. However, other means as illustrated in FIGS. 7A-7D may be adopted.

Figure 7A:
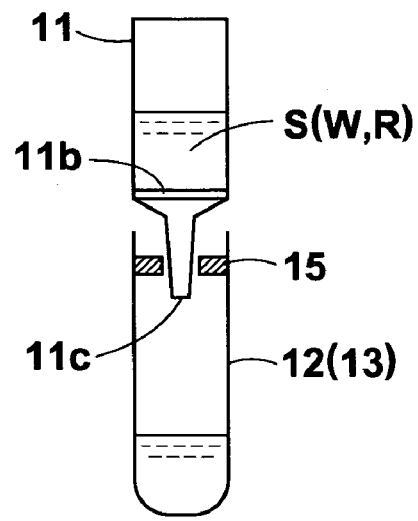
FIG. 7A illustrates another example of a discharged liquid scattering prevention means.

FIG. 7A illustrates an example where a ring 15 for preventing scattering is provided at an opening of the waste liquid vessel 12 or the recovery vessel 13. The scattering of the discharged liquid can be prevented by covering the opening by inserting the discharging bottom end 11c of the extracting cartridge 11 to the inner hole of the ring 15.

Figure 7B:
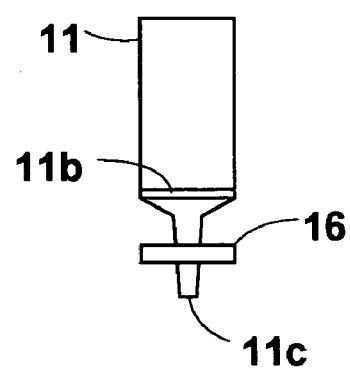
FIG. 7B illustrates another example of a discharged liquid scattering prevention means.

FIG. 7B illustrates an example where a ring 16 for preventing scattering is provided at the discharging bottom end 11c of the extracting cartridge 11. The scattering of the discharged liquid can be prevented by covering the opening of the waste liquid vessel 12 or the recovery vessel 13 with the ring 16.

Figure 7C:
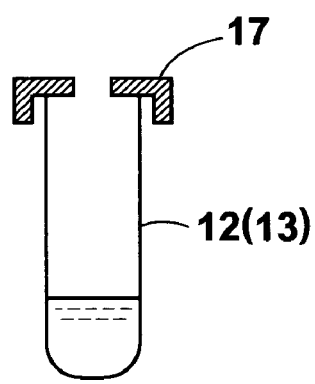
FIG. 7C illustrates another example of a discharged liquid scattering prevention means.

FIG. 7C illustrates an example where a ring 17 for preventing scattering, which is in a shape of a cap, is provided at an opening of the waste liquid vessel 12 or the recovery vessel 13. The scattering of the discharged liquid can be prevented by covering the opening by inserting the discharging bottom end 11c of the extracting cartridge 11 to the inner hole of the ring 17.

Figure 7D:
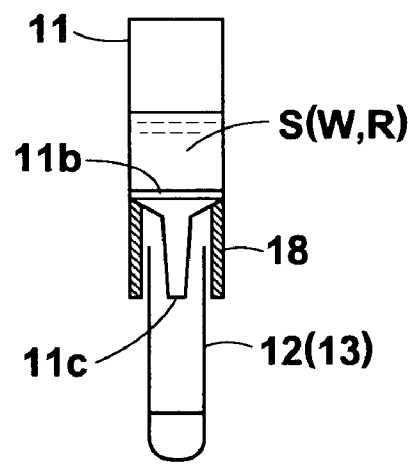
FIG. 7D illustrates another example of a discharged liquid scattering prevention means.

FIG. 7D illustrates an example where a cylinder member 18 for preventing scattering is provided at the outer circumference of the discharging bottom end 11c of the extracting cartridge 11. The scattering of the discharged liquid can be prevented by covering the outer circumference of the opening of the waste liquid vessel 12 or the recovery vessel 13 with the cylinder member 18.

The aforementioned rings 15-17 and cylinder member 18 may be formed integrally with the waste liquid vessel 12 or the recovery vessel 13. However, preferably, the rings and the cylinder member should be formed separately from the waste liquid vessel 12 or the recovery vessel 13 in a detachable manner.

In the embodiment described above, the plurality of the extracting cartridges 11, 11, . . . are loaded. However, the nucleic acid extracting apparatus in accordance with the present invention is not limited to the use of the plurality of the extracting cartridges 11, 11, . . . and is applicable also in cases where only one extracting cartridge 11 is used.

In the present embodiment, the washing processing is performed by the use of the washing liquid W. However, the washing processing is not always required depending on the filtering performance of the filter member 11b.

Further, in the embodiment as described above, the nucleic acid extracting apparatus is described. However, the present invention is not limited to the nucleic acid extracting apparatus. The present invention may also be adopted to a method for filtering various kinds of predetermined substance through contact with the filter member. Further, it is not necessary to recover the recovery liquid. The predetermined substance can be kept in contact with the filter member during analysis. A liquid for analyzing the reaction color may also be added.

What is claimed is:

1. An extracting apparatus for performing an extracting operation, the apparatus comprising:
    at least one extracting cartridge provided with a filter member which extracts a component from a sample liquid;
    a loading mechanism for holding the at least one extracting cartridge, at least one waste liquid vessel for accommodating a discharged liquid of the sample liquid, and at least one recovery vessel for accommodating a recovery liquid, which contains the extracted component;
    a pressurized air supplying mechanism, vertically moveable with respect to the at least one extracting cartridge by an element fitted to a means for adjusting position of the at least one extracting cartridge, for introducing pressurized air into the at least one extracting cartridge; and
    a liquid injecting mechanism for injecting the recovery liquid into the at least one extracting cartridge.

2. An apparatus as defined in claim 1 wherein the loading mechanism comprises:
    a) a stand, which is loaded on an apparatus main body,
    b) a cartridge holder, which is supported for vertical movement by the stand and holds the at least one extracting cartridge, and
    c) a vessel holder, which holds the at least one waste liquid vessel and the at least one recovery vessel at positions below the cartridge holder such that the position of the at least one waste liquid vessel with respect to the at least one extracting cartridge and the position of the at least one recovery vessel with respect to the at least one extracting cartridge are capable of being changed over.

3. An apparatus as defined in claim 1 wherein the pressurized air supplying mechanism comprises:
    a) at least one air nozzle, which jets out pressurized air from a bottom end,
    b) a pressurizing head, which supports the at least one air nozzle and vertically moves the at least one air nozzle with respect to the at least one extracting cartridge having been held by the cartridge holder, and
    c) position adjusting means, which is fitted to the pressurizing head and adjusts the position of the at least one extracting cartridge in a rack of the loading mechanism.

4. An apparatus as defined in claim 1 wherein the liquid injecting mechanism comprises:
    a) a recovery liquid injecting nozzle, from which the recovery liquid is injected into the at least one extracting cartridge,
    b) a nozzle moving base, which holds the recovery liquid injecting nozzle and is capable of moving above the at least one extracting cartridge having been held by the loading mechanism, and
    c) a recovery liquid supplying pump, which sucks up the recovery liquid from a recovery liquid bottle that accommodates the recovery liquid therein, and which supplies the recovery liquid into the recovery liquid injecting nozzle.

5. An apparatus as defined in claim 1 wherein the loading mechanism comprises:
    a) a stand, which is loaded on an apparatus main body,
    b) a cartridge holder, which is supported for vertical movement by the stand and holds the at least one extracting cartridge, and
    c) a vessel holder, which holds the at least one waste liquid vessel and the at least one recovery vessel at positions below the cartridge holder such that the position of the at least one waste liquid vessel with respect to the at least one extracting cartridge and the position of the at least one recovery vessel with respect to the at least one extracting cartridge are capable of being changed over,
the pressurized air supplying mechanism comprises:
    a) at least one air nozzle, which jets out pressurized air from a bottom end,
    b) a pressurizing head, which supports the at least one air nozzle and vertically moves the at least one air nozzle with respect to the at least one extracting cartridge having been held by the cartridge holder, and
    c) position adjusting means, which is fitted to the pressurizing head and adjusts the position of the at least one extracting cartridge in a rack of the loading mechanism, and
the liquid injecting mechanism comprises:
    a) a recovery liquid injecting nozzle, from which the recovery liquid is injected into the at least one extracting cartridge,
    b) a nozzle moving base, which holds the recovery liquid injecting nozzle and is capable of moving above the at least one extracting cartridge having been held by the loading mechanism, and
    c) a recovery liquid supplying pump, which sucks up the recovery liquid from a recovery liquid bottle that accommodates the recovery liquid therein, and which supplies the recovery liquid into the recovery liquid injecting nozzle.

6. An apparatus as defined in claim 5, further comprising:
    a scattering prevention means to prevent scattering of a discharge liquid from a discharge bottom end of the extracting cartridge,
    wherein the scattering prevention means to prevent scattering of the discharged liquid is a means for inserting the discharging bottom end of the at least one extracting cartridge by a predetermined length into the at least one waste liquid vessel.

7. An apparatus as defined in claim 1 wherein the predetermined substance is a nucleic acid.

8. An apparatus as defined in claim 7 wherein the filter member of the at least one extracting cartridge is constituted of a porous film capable of adsorbing the nucleic acid with an interaction other than interactions in which an ionic bond takes part.

9. An apparatus as defined in claim 7 wherein the filter member of the at least one extracting cartridge is constituted of a porous film of an organic material having a hydroxyl group.

10. An apparatus as defined in claim 7 wherein the filter member of the at least one extracting cartridge is constituted of a porous film of a mixture of acetylceluloses having different acetyl values.

11. An apparatus as defined in claim 7 wherein the filter member of the at least one extracting cartridge is constituted of a porous film of a regenerated cellulose.

12. An apparatus as defined in claim 7 wherein the filter member of the at least one extracting cartridge is constituted of a porous film of an organic material obtained from saponification of a mixture of acetylcelluloses having different acetyl values.

13. An apparatus as defined in claim 7 wherein the filter member of the at least one extracting cartridge is constituted of a porous film of an inorganic material containing a silica compound.

14. An apparatus as defined in claim 7 wherein the filter member is a glass filter.

15. An extracting apparatus for performing an extracting operation, the apparatus comprising:

an extracting cartridge provided with a filter member which extracts a component from a sample liquid;

a loading mechanism for holding the extracting cartridge, a waste liquid vessel for accommodating a discharged liquid of the sample liquid, and a recovery vessel for accommodating a recovery liquid, which contains the extracted component;

a pressurized air supplying mechanism, vertically movable with respect to the at least one extracting cartridge by an element fitted to a means for adjusting position of the extracting cartridge, for introducing pressurized air into the extracting cartridge; and a liquid injecting mechanism for injecting the recovery liquid into the extracting cartridge.

* * * * *